United States Patent

Keller et al.

[11] Patent Number: 5,347,015
[45] Date of Patent: Sep. 13, 1994

[54] DISULFIDES

[75] Inventors: Harald Keller, Ludwigshafen; Wolfgang Schrepp, Heidelberg; Harald Fuchs, Carlsberg, all of Fed. Rep. of Germany

[73] Assignee: BASF Aktiengesellschaft, Ludwigshafen, Fed. Rep. of Germany

[21] Appl. No.: 932,995

[22] Filed: Aug. 20, 1992

[30] Foreign Application Priority Data

Aug. 23, 1991 [DE] Fed. Rep. of Germany ....... 4127821

[51] Int. Cl.$^5$ .................. C07D 403/12; C07C 309/66; C07C 309/64
[52] U.S. Cl. .................................. 548/455; 560/154; 558/46; 558/60; 564/500; 568/22; 568/24
[58] Field of Search .................... 548/455; 558/46, 60; 560/154; 564/500; 568/22, 24

[56] References Cited

PUBLICATIONS

J. Phys. Chem. 86, 2700-04 (1982), Allara et al.
Houben-Weyl, Bd. 9, 55-82 (1955), Schoberl et al.
J. Am. Chem. Soc. 111, 321-35 (1989), Bain et al.
Angew. Chem. 101, 522-29 (1989) Bain et al.

*Primary Examiner*—David B. Springer
*Attorney, Agent, or Firm*—Keil & Weinkauf

[57] ABSTRACT

Disulfides of the general formula $$X^1-(CH_2)_n-S-S-(CH_2)_n-X^2$$

where $X^1$ and $X^2$ are identical to one another and are each $-Br$, $-N$-phthalimide, $-NH_2$, $-OOC-(CH_2)_3-COOH$, $-OSO_2-CH_3$, $-NH-(CH_2)_2-NH_2$, $-SO_3H$ or $-SO_3^-M^+$ in which $M^+$ is an alkali metal ion and n is from 11 to 25, or $X^1$ is $-OH$ and $X^2$ is $-Br$ or $X^1$ and $X^2$ are each $-COO-CH_2-CH_3$ and n is from 10 to 25, are suitable for the production of monomolecular layers on noble metal substrates and for the production of multimolecular layers.

2 Claims, No Drawings

DISULFIDES

The present invention relates to novel organic disulfides, their preparation and the preparation of chemisorbed disulfide films onto noble metal substrates.

The modification of substrate surfaces is wide-spread in industrial technology. Protection from abrasion or fading and corrosion protection are examples of material protection by special coatings. In the optical industry, surface modifications are widely used in frequency filters and reflectors. The modification of surfaces at the molecular level, for example by applying monomolecular layers, has only been intensively investigated and developed in recent years. Thus, it is known that organic disulfides and thiols are spontaneously chemisorbed from solution onto gold and silver surfaces. After rinsing with a solvent, stable monomolecular films are obtained on the metal substrate. Terminal functional groups of the disulfide or thiolate films influence the wettability of the coated metal surface (cf. C. D. Bain, E. B. Troughton, Y. T. Tao, J. Evall, G. M. Whitesides and R. G. Nuzzo, J. Am. Chem. Soc. 111 (1989), 321, C. J. Sandroff and D. R. Hershbach, J. Phys. Chem. 86 (1982), 2700, and C. D. Bain and G. M. Whitesides, Angew. Chem. 101 (1989), 522).

Organic disulfides having terminal functional groups are known but in particular short-chain disulfides having terminal functional groups have been synthesized in the past. Disulfides can be synthesized by various methods, for example by the oxidation of thiols, nucleophilic substitution by means of $(S—S)^{2-}$ and oxidation of Bunte salts (cf. E. Müller, Methoden der Organischen Chemie, Houben-Weyl, Vol. 9, 55–82 (1955)).

Short-chain disulfides have the disadvantage that, as monomolecular films, they have no possibility of two-dimensional crystallization. Consequently, such films are not dense and furthermore do not have a high degree of order. In addition, the mechanical and thermal stability of short-chain disulfide films is lower than that of the films of long-chain disulfides.

It is an object of the present invention to provide disulfides which can be prepared in a reproducible manner and have the following advantages:

a) As monomolecular chemisorbed layers, they should form very dense films and thus ensure corrosion protection.

b) As monomolecular chemisorbed layers, they should expose a large number of terminal functional groups at the surface and thus permit the chemical bonding of further layers and the selective modification of wetting properties.

We have found, surprisingly, that this object is achieved by the novel long-chain disulfides.

The present invention relates to disulfides of the general formula (I)

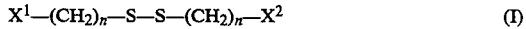

$$X^1—(CH_2)_n—S—S—(CH_2)_n—X^2 \qquad (I)$$

where $X^1$ and $X^2$ are identical to one another and are each —Br, phthalimido, —NH$_2$, —OOC—(CH$_2$)$_3$—COOH, —OSO$_2$—CH$_3$, —NH—(CH$_2$)$_2$—NH$_2$, —SO$_3$H or —SO$_3^-$M$^+$ in which M$^+$ is Li$^+$, Na$^+$ or K$^+$, and n is an integer from 11 to 25, or $X^1$ is —OH and $X^2$ is —Br and n is from 11 to 25, or $X^1$ and $X^2$ are each —COO—CH$_2$—CH$_3$ and n is from 10 to 25.

Preferred disulfides of the general formula (I) are those in which n is from 11 to 13.

The present invention furthermore relates to the following processes for the preparation of the novel disulfides, i.e. a process for the preparation of the disulfides of the general formula (I), $X^1$—(CH$_2$)$_n$—S—S—(CH$_2$)$_n$—X$^2$, where $X^1$ and $X^2$ are identical to one another and are each —Br, —OOC—(CH$_2$)$_3$—COOH or —OSO$_2$—CH$_3$ or $X^1$ is —OH and $X^2$ is —Br, wherein, in a first synthesis step, a terminally bromine-substituted alcohol of the formula Br—(CH$_2$)$_n$—OH, where n is from 11 to 25, is reacted with an equimolar amount of sodium thiosulfate in water or in a polar organic solvent at from 60° to 120° C. to give the Bunte salt, in the second synthesis step the solution of the Bunte salt is oxidized with iodine to the disulfide, in the third synthesis step the disulfide is treated with hydrogen bromide at from 60° to 120° C., both the monosubstitution product ($X^1$=—OH, $X^2$=—Br) and the disubstitution product ($X^1$=$X^2$=—Br) being formed, and the two differently substituted disulfides are separated, where $X^1$ and $X^2$ in the formula (I) are each —OOC—(CH$_2$)$_3$—COOH the product of the second synthesis step being reacted in the third synthesis step with glutaric anhydride at from about 70° to 120° C. to give the corresponding half ester of glutaric acid and, if necessary, then being purified by crystallization, and where $X^1$ and $X^2$ in the formula (I) are each —OSO$_2$—CH$_3$ the product of the second synthesis step being reacted in the third synthesis step with methanesulfonyl chloride at from 0° to 20° C. in an anhydrous aprotic organic solvent in the presence of a tertiary amine, the resulting amine hydrochloride being removed and the disulfide in which $X^1$ and $X^2$ are each —O—SO$_2$—CH$_3$ being obtained from the remaining solution after evaporation of the solvent; also a process for the preparation of the disulfides of the general formula (I), where $X^1$ and $X^2$ are identical to one another and are each —NH—(CH$_2$)$_2$—NH$_2$, wherein the disulfide prepared by the above process and in which $X^1$ and $X^2$ are each —O—SO$_2$—CH$_3$ is reacted with excess ethylenediamine at from 50° to 100° C. and the product is, if required, purified; furthermore a process for the preparation of the disulfides of the general formula (I), where $X^1$ and $X^2$ are identical to one another and are each phthalimido, wherein, in a first synthesis step, a terminally bromine-substituted alcohol of the formula Br—(CH$_2$)$_n$—OH in which n is from 11 to 25 is reacted with an equimolar amount of potassium phthalimide in a polar aprotic solvent at from 50° to 100° C., the reaction product is obtained by precipitation in water and if necessary purified by recrystallization, the product thus obtained is heated in a second synthesis step with an excess of concentrated aqueous hydrogen bromide solution and concentrated sulfuric acid to 60°–120° C., and the product precipitated at room temperature is, if required, purified by recrystallization, in a third synthesis step an equimolar amount of sodium thiosulfate is added and the mixture is heated in water or in a polar organic solvent or a mixture thereof to 60°–120° C., and the product thus obtained is, if required, purified by recrystallization and, in a fourth synthesis step, is dissolved in a protic organic solvent and is oxidized with iodine and, if required, purified by recrystallization.

The process for the preparation of the disulfides of the general formula (I), where $X^1$ and $X^2$ are identical to one another and are each —NH$_2$, comprises treating the product prepared by the above process with excess hydrazine in a polar organic solvent at room temperature, bringing the resulting precipitate into solution by adding aqueous alkali metal hydroxide solution, extracting the product with ether and purifying by recrystallization the crude product obtained after evaporation of the ether.

The process for the preparation of the disulfides of the general formula (I), where $X^1$ and $X^2$ are identical to one another and are each —COO—$CH_2$—$CH_3$, comprises, in a first synthesis step, heating a terminally bromine-substituted carboxylic acid of the formula Br—$(CH_2)_n$—COOH in which n is from 10 to 25 with an equimolar amount of sodium thiosulfate in a mixture of a polar organic solvent and water to 60°–120° C. and, in a second synthesis step, dissolving the product obtained in crystalline form on cooling, which may have been recrystallized, in boiling ethanol and oxidizing it with the semimolar amount of iodine to give the disulfide, neutralizing the resulting hydrogen iodide and, if required, recrystallizing the product obtained.

The process for the preparation of disulfides of the general formula (I), where $X^1$ and $X^2$ are identical to one another and are each —$SO_3^-M^+$, e.g. —$SO_3^-Na^+$, comprises, in a first synthesis step, reacting a terminally bromine-substituted alcohol of the formula Br—$(CH_2)_n$—OH in which n is from 11 to 25 with an equimolar amount of sodium sulfite, dissolved in water, at from 80° to 120° C., in a second synthesis step heating the product obtained on cooling, which may have been recrystallized, with an excess of an aqueous concentrated hydrogen bromide solution and concentrated sulfuric acid to 60°–120° C., and in a third synthesis step reacting the product precipitated on cooling, which may have been recrystallized, with an equimolar amount of sodium thiosulfate in water at from 80° to 120° C., adding the semimolar amount of iodine, dissolved in a polar organic solvent, dropwise to the boiling solution of this reaction product, then neutralizing with sodium carbonate and if necessary recrystallizing from water the product precipitated on cooling.

Disulfides of the general formula (I), where $X^1$ and $X^2$ are identical to one another and are each —$SO_3H$, are obtained by a method in which a disulfide having an —$SO_3Na$ group and obtainable by the above process is boiled in excess concentrated mineral acid and the solid precipitated on cooling is, if required, recrystallized from water.

The present invention furthermore relates to a process for the production of monomolecular layers on noble metal substrates using the novel disulfides, wherein the noble metal substrate is brought into contact with a solution of the novel disulfide, with the result that chemisorption of the disulfide on the noble metal substrate takes place.

The present invention also relates to a process for the production of multimolecular layers on substrates whose surface has been modified by applying novel disulfide layers by the above process, wherein the multimolecular layers are built up sequentially, i.e. layer by layer, and the individual layers are chemically bonded to one another.

The adhesion of the novel disulfides to the noble metal substrate is by covalent bonding via the sulfur to the metal. These are therefore chemisorbed disulfide films.

The long unbranched alkyl chains of the novel disulfide produce two-dimensional crystallization within the disulfide monolayer. This crystallization imparts higher thermal and mechanical stability to the film and makes it more impermeable to the diffusion of small particles through the film. Dense monomolecular disulfide films are corrosion inhibitors, as shown by electrochemical impedance spectroscopy (EIS). The two-dimensional crystallization, due to long unbranched alkyl chains of the disulfides, furthermore increases the degree of order within the monomolecular layer. The high degree of order results in exposure of the terminal functional groups of the disulfide film at the surface. Consequently, by choosing suitable functional groups, it is possible selectively to modify the wettability of the surface. The functional groups may furthermore be used for the selective chemical synthesis of further layers.

Regarding the novel disulfides, their preparation and their use, the following may be stated specifically.

The novel disulfides of the general formula (I)

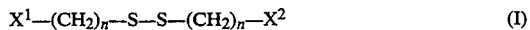

$$X^1-(CH_2)_n-S-S-(CH_2)_n-X^2 \qquad (I)$$

contain long-chain alkylene radicals in which n is from 11 to 25, preferably from 11 to 13; where $X^1$ and $X^2$ are identical to one another, they are the substituents —Br, phthalimido, —$NH_2$, —OOC—$(CH_2)_3$—COOH, —$OSO_2$—$CH_3$, —NH—$(CH_2)_2$—$NH_2$, —$SO_3H$ or —$SO_3^-M^+$ in which $M^+$ is $Li^+$, $Na^+$ or $K^+$; however, $X^1$ and $X^2$ may also differ from one another and are then —Br and —OH; where $X^1$ and $X^2$ are identical to one another and are each —COO—$CH_2$—$CH_3$, n may be an integer from 10 to 25.

Examples of radicals —$(CH_2)_n$— are undecanediyl, dodecanediyl, tridecanediyl, tetradecanediyl, pentadecanediyl, hexadecanediyl, heptadecanediyl, octadecanediyl, nonadecanediyl, eicosanediyl, tetracosanediyl and pentacosanediyl, undecanediyl, dodecanediyl and tridecanediyl being preferred.

Where $X^1$ and $X^2$ are identical to one another and are each —Br, —OOC—$(CH_2)_3$—COOH or —$OSO_2$—$CH_3$ and where $X^1$ is —OH and $X^2$ is —Br, the novel disulfides of the general formula (I) can be prepared by a process in which, in a first synthesis step, a correspondingly terminally bromine-substituted alcohol of the formula Br—$(CH_2)_n$—OH in which n is from 11 to 25 is reacted with an equimolar amount or with a slight excess of sodium thiosulfate in water or in a polar organic solvent, e.g. methanol, ethanol, isopropanol, butanol or ethylene glycol, or a mixture thereof with water at from 60° to 120° C., preferably at the boiling point of the solvent used, to give the Bunte salt, the solution of which, for example in boiling ethanol, is oxidized with iodine in a second synthesis step to give the disulfide. Where $X^1$ and $X^2$ are each —Br and where $X^1$ is —OH and $X^2$ is —Br, the disulfide is then treated in a third synthesis step at from 60° to 120° C. with hydrogen bromide, for example stirred with aqueous hydrogen bromide solution under reflux, both the monosubstitution product ($X^1$=—OH, $X^2$=—Br) and the disubstitution product ($X^1$=$X^2$=—Br) being formed. The differently substituted disulfides obtained in this manner can be separated and purified by column chromatography (for example using silica gel).

Where $X^1$ and $X^2$ in the general formula (I) are each —OOC—$(CH_2)_3$—COOH, the product obtained in the second synthesis step is reacted, in the third synthesis step, with glutaric anhydride at from about 70° to 2120° C., for example by stirring for about one hour at 90° C., to give the corresponding half ester of glutaric acid, which can, if required, be further purified by recrystallization.

Where $X^1$ and $X^2$ in the general formula (I) are each —O—SO$_2$—CH$_3$, the disulfide obtained in the second synthesis step is reacted, in a third synthesis steps with methanesulfonyl chloride at from 0° to 20° C., preferably at 0° C., in an anhydrous aprotic organic solvent in the presence of a tertiary amine, for example triethylamine. The solution thus obtained can be stirred for a further two hours at room temperatures, the resulting amine hydrochloride is then removed by filtration and the filtrate then extracted by shaking with the same amount of water. The novel disulfide in which $X^1$ and $X^2$ are each —O—SO$_3$—CH$_3$ is obtained as a solid substance from the organic phase after evaporation of the solvent and may be further purified by recrystallization.

For the preparation of novel disulfides in which $X^1$ and $X^2$ are each —NH—CH$_2$—CH$_2$—NH$_2$, the disulfides in which $X^1$ and $X^2$ are each —O—SO$_2$—CH$_3$ can be reacted with excess ethylenediamine at from 50° to 100° C., for example by refluxing the stirred ethanolic solution for about three hours. The ethanol can then be removed in a rotary evaporator, the residue taken up in dichloromethane and the solution extracted twice by shaking with water. The disulfide having —NH—CH$_2$—CH$_2$—NH$_2$ terminal groups is then obtained from the organic phase and can be purified by recrystallization, for example from hexane.

For the preparation of novel disulfides in which $X^1$ and $X^2$ are each phthalimido, in a first synthesis step a terminally bromine-substituted alcohol of the formula Br—(CH$_2$)$_n$—OH in which n is from 11 to 25 is reacted with an equimolar amount of potassium phthalimide in a polar aprotic organic solvent, e.g. dimethylformamide, at from 50° to 100° C., for example by stirring for three hours at 70° C. The reaction product is precipitated by pouring its solution into twice the amount of water and can be further purified by recrystallization from a heptane/ethanol mixture. The product thus obtained can be treated, in a second synthesis step, with an excess of concentrated aqueous hydrogen bromide solution, for example three times the amount of 47% strength aqueous hydrogen bromide solution, and concentrated sulfuric acid, for example an equimolar amount of concentrated sulfuric acid, at from 60° to 120° C., for example by refluxing for four hours. The product precipitated on cooling to room temperature can be further purified by recrystallization, for example from hexane. In a third synthesis step, the product thus obtained, dissolved in a protic organic solvent, for example in boiling ethanol, can be reacted with an equimolar amount or a slight excess of sodium thiosulfate and heated in water or in a polar organic solvent or a mixture thereof with water, for example in a mixture of water and ethanol, to 60°–120° C., for example by refluxing for six hours. The product thus obtained can be further purified by recrystallization, for example from ethanol. In a fourth synthesis step, this product can be dissolved in a protic organic solvent, for example in boiling ethanol, and oxidized with the semimolar amount of iodine, and, if required, purified by recrystallization. After the end of the addition of iodine, it may be advantageous to reflux the stirred mixture for about a further 15 minutes, to neutralize it with sodium carbonate and to remove an iodine color by adding sodium disulfite. The product which crystallizes at room temperature can be recrystallized from a mixture of heptane and ethyl acetate.

For the preparation of the novel disulfides of the general formula (I) where $X^1$ and $X^2$ are each NH$_2$, the disulfide prepared by the above process and containing terminal phthalimido groups is treated with excess hydrazine in a polar organic solvent, e.g. ethanol, at room temperature, for example while stirring tile reaction mixture for five hours. The resulting precipitate is brought into solution by adding aqueous alkali metal hydroxide solution, for example 10% strength sodium hydroxide solution, and the product is extracted with ether. The product remaining after evaporation of the ether can be further purified by recrystallization from hexane.

For the preparation of the novel disulfides of the general formula (I) where $X^1$ and $X^2$ are each —COO—CH$_2$—CH$_3$, in a first synthesis step a terminally bromine-substituted carboxylic acid of the formula Br—(CH$_2$)$_n$—COOH in which n is from 10 to 25 is heated with an equimolar amount or a slight excess of sodium thiosulfate in a mixture of a polar organic solvent, e.g. ethanol, and water to 60°–120° C., for example by refluxing for three hours. The crystalline product obtained on cooling can be recrystallized from ethanol for further purification. In a second synthesis step, this product is dissolved in boiling ethanol and oxidized with the semimolar amount of iodine to give the disulfide. The resulting hydrogen iodide is advantageously neutralized. The product thus obtained can be recrystalized from methanol for further purification.

For the preparation of the novel disulfides of the general formula (I) where $X^1$ and $X^2$ are each —SO$_3$Na, in a first synthesis step a terminally bromine-substituted alcohol of the formula Br—(CH$_2$)$_n$—OH where n is from 11 to 25 is reacted with an equimolar amount of sodium sulfite dissolved in water, at from 80° to 120° C., for example by refluxing for ten hours. The product obtained on cooling the reaction solution can be recrystallized from water for further purification. In a second synthesis step, this product is heated with an excess of aqueous concentrated hydrogen bromide solution and concentrated sulfuric acid, preferably an equimolar amount, to 60°–120° C., for example by refluxing for five hours. The product precipitated on cooling can be recrystallized from ethanol for further purification. In a third synthesis step, this product is reacted with an equimolar amount or a slight excess of sodium thiosulfate in water at from 80° to 120° C. for example by refluxing for five hours. The semimolar amount of iodine, dissolved in a polar organic solvent, e.g. ethanol, is added to the boiling solution of this reaction product, neutralization is then effected with sodium carbonate and the product precipitated on cooling is, if required, recrystallized from water.

By briefly boiling the novel disulfide of the general formula (I) where $X^1$ and $X^2$ are each —SO$_3$—Na in excess concentrated mineral acid, for example hydrochloric acid, disulfides of the general formula (I) where $X^1$ and $X^1$ are each —SO$_3$H are obtained on cooling and can be recrystallized from water.

As stated above, the novel disulfides can be very advantageously used for the production of chemisorbed monomolecular layers on noble metal surfaces.

Suitable substrates for monomolecular layers consisting of disulfides are noble metal surfaces, for example gold, silver, platinum or palladium surfaces, ultrathin coatings of these metals, consisting of a few atomic layers, on other substrates also being sufficient for producing the disulfide layer. Formation of a covalent or coordinate bond between the disulfide and metal atoms of the substrate surface is important for the production of a disulfide layer. The disulfide layers are preferably produced by immersing the substrate in a solution of the disulfide and then washing off the excess non-chemisorbed disulfide material with the pure solvent. By immersion in solutions of a mixture of a plurality of disulfides, mixed disulfide films can be produced. Instead of immersing the substrates in disulfide solutions, the substrates may also be sprayed with disulfide solutions or brought into contact with the disulfides in another manner. The process for the production of the disulfide layers is independent of the type of solvent. The solvent should merely ensure adequate solubility of the disulfides.

The monomolecular disulfide layers produced according to the invention (first layer) have exposed functional groups at the surface. These functional groups permit the production of a second layer by chemical reaction. If the second layer in turn has functional groups at the surface, a third layer can be produced by chemical reaction. Multimolecular layers can be produced by this principle. There is in principle no limit to the number of layers.

Multimolecular layers produced according to the invention (multilayers) comprise two or more monomolecular layers of different materials which are bonded to one another chemically, i.e. by covalent, ionic or coordinate bonds.

The multilayers are produced layer by layer by successive immersion in solutions of the layer-forming materials. Washing with a pure solvent is advantageously effected between the immersion operations, in order to remove excess layer-forming material.

The simplest multilayer structure thus corresponds to the type ABABAB..., but more complex multilayer systems, for example of the type ABCDCBABC... or ABCBCDC..., may also be produced by using more than two layer-forming materials, A containing functional groups which react with B, B containing functional groups which react with A and C, C containing functional groups which react with B and D, and D containing functional groups which react with C.

In choosing the functional groups, it is important that the functional groups of the subsequent layer react chemically with the functional groups of the preceding layer, and a chemical bond, for example a covalent, ionic or coordinate one, is formed by the reaction. This ensures good and permanent adhesion of the multilayer systems, high thermal and mechanical stability and high resistance to solvents and chemicals.

To produce multilayers having 3 or more layers, bi- or polyfunctional substances are required as layer-forming materials since one functional group reacts with the preceding layer and a further functional group with the subsequent layer and in this way the individual layers are chemically bonded to one another.

The use of bi- or polyfunctional substances for producing multilayers having 3 or more layers can be avoided by means of an artifice, by using monofunctional cyclic substances which react with the preceding layer to produce a new functional group simultaneously by a ring cleavage reaction. This new functional group can react with the subsequent layer. Suitable monofunctional cyclic substances are in particular cyclic anhydrides, for example glutaric, succinic and maleic anhydride, sultones, such as 1,3-propanesultone, 1,4-butanesultone, etc., and cyclic reactive ethers, thioethers and amines, such as ethylene oxide, ethylene sulfide and ethyleneamine.

If the functional groups of the preceding layer do not react spontaneously with the subsequent layer, they may be activated by suitable chemicals. For example, carboxyl groups can be activated by means of thionyl chloride, oxalyl dichloride, carbodiimides and the like to react with nucleophilic groups of the subsequent layer.

1) Possible functional groups for producing the second layer:

The functional groups of the first layer are predetermined by the use of the novel disulfides.

1a) If the first layer (disulfide layer) has terminal nucleophilic groups ($X^1$ or $X^2$=—$NH_2$, —NH—$(CH_2)_2$—$NH_2$ or —OH), suitable substances for producing the second layer are those which carry electrophilic groups, for example anhydride, acyl chloride, aldehyde, alkyl halide, sulfonic ester, sulfuric ester, isocyanate, isothiocyanate, acrylate, acrylamido, maleimido, vinylsulfonyl, epoxy and similar groups.

1b) If the first layer has terminal basic groups, for example amino groups ($X^1$ or $X^2$=—$NH_2$ or —NH—$(CH_2)_2$—$NH_2$), suitable substances for producing the second layer are those which contain acid groups, for example HOOC—, $HO_3S$—, $HO_3SO$—, $H_2O_3P$— and $H_2O_3PO$— groups.

1c) If the first layer has terminal electrophilic groups ($X^1$ or $X^2$=—Br or —$OSO_2$—$CH_3$), substances which are suitable for producing the second layer are those which have nucleophilic groups, for example amino, hydroxyl, mercapto, carban-ion or phosphine groups.

1d) If the first layer has terminal $HO_3S$— groups or HOOC—$(CH_2)_3$—COO— groups, suitable substances for producing the second layer are those which have basic groups, for example amino, amidino, guanidino or S-alkylthiourea groups. If the $HO_3S$— or HOOC—$(CH_2)_3$—COO— groups are activated with thionyl chloride, oxalyl dichloride, carbodiimides or the like, nucleophilic groups such as those stated under 1c) are suitable for producing the second layer.

1e) If the first layer has terminal $NaO_3S$— groups, substances which are suitable for producing the second layer are those which have cationic groups, for example ammonium, amidinium, guanidinium, isothiuronium and phosphonium groups.

2) Possible functional groups for producing the third and further layers:

2a) If the preceding layer has terminal nucleophilic groups, substances having electrophilic groups, as stated for example under 1a), are suitable for producing the following layer.

2b) If the preceding layer has terminal basic groups, for example amino, amidino, guanidino or S-alkylthiourea groups, substances which contain acid groups, for example HOOC—, $HO_3S$—, $HO_3SO$—, $H_2O_3P$— and $H_2O_3PO$— groups, are suitable for producing the following layer.

2c) If the preceding layer has terminal electrophilic groups, substances which have nucleophilic groups, for example amino, hydroxyl, mercapto, carbanion and phosphine groups, are suitable for producing the second layer.

2d) If the preceding layer has acid groups, for example HOOC—, $HO_3S$—, $HO_3SO$—, $H_2O_3P$— and $H_2O_3PO$-groups, substances having basic groups, for example amino, amidino, guanidino and S-alkyl thiourea groups, are suitable for producing the following layer.

In addition to their use as the first layer for a subsequent multilayer structure, monomolecular disulfide layers are employed as ultrathin glide layers, for example for magnetic recording media, and as ultrathin corrosion prevention layers on silver or gold surfaces.

By producing multimolecular layers, according to the invention, on electrodes, quartz resonators, surface wave components or optical components, it is possible to tailor their properties. For example, one or more layers of the multilayer structure may represent receptors for biological molecules and may therefore be used as biosensors. Layers which contain chemical receptors (crown ethers, cryptands) are used as chemical sensors, especially gas sensors and ion sensors.

Multilayer systems which contain chromophores can act as optical switches or frequency doublers by utilizing nonlinear optical effects.

In the Examples which follow, parts and percentages are by weight, unless stated otherwise.

EXAMPLE 1 a) Preparation of compound (1) according to the equation

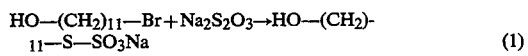

$$\text{HO—(CH}_2)_{11}\text{—Br} + \text{Na}_2\text{S}_2\text{O}_3 \rightarrow \text{HO—(CH}_2)_{11}\text{—S—SO}_3\text{Na} \quad (1)$$

200 g of water and 160 g of ethanol are added to 50 g (0.199 mol) of 11-bromoundecanoic acid and 49.4 g (0.199 mol) of sodium thiosulfate pentahydrate, and the mixture is refluxed for 4 hours. The crude product separates out in crystalline form on cooling, and is filtered off under suction, dried under reduced pressure and recrystallized from 880 g of ethanol. The yield is 48.3 g (81%) of colorless crystals.

Identification: TLC (thin layer chromatography); IR and $^1$H-NMR spectrum; melting point: 181°–183° C.

b) Preparation of compound (2) according to the equation

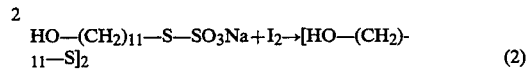

$$2 \text{ HO—(CH}_2)_{11}\text{—S—SO}_3\text{Na} + \text{I}_2 \rightarrow [\text{HO—(CH}_2)_{11}\text{—S}]_2 \quad (2)$$

84 g of ethanol and 50 g of water are added to 31.5 g (103 mmol) of compound (1). The mixture is heated to the boil, and a solution of 13.05 g (51.4 mmol) of iodine in 116 g of ethanol is slowly added dropwise. Neutralization is then effected with sodium carbonate, and the iodine color of the solution is eliminated by adding aqueous sodium disulfite solution. The crude product separates out in crystalline form on cooling and is filtered off under suction and recrystallized from 80 g of methanol.

Yield: 17.9 g (86%) of colorless crystals.

Identification: TLC; IR and $^1$H-NMR spectrum; melting point: 79°–81° C.

Elemental analysis:
Calculated C 64.97% H 11.40% S 15.77%;
found C 64.90% H 11.30% S 15.80% c) Preparation of the novel compounds (3) and (4) according to the equation

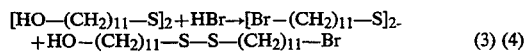

$$[\text{HO—(CH}_2)_{11}\text{—S}]_2 + \text{HBr} \rightarrow [\text{Br—(CH}_2)_{11}\text{—S}]_2 + \text{HO—(CH}_2)_{11}\text{—S—S—(CH}_2)_{11}\text{—Br} \quad (3)(4)$$

2 g (4.92 mmol) of compound (2), 3.81 g (14.76 mmol) of 47 percent strength aqueous hydrogen bromide solution and 0.62 g (6.32 mmol) of concentrated sulfuric acid are refluxed for 5 hours. An educt is no longer detectable in the thin layer chromatogram (TLC). Brown crystals separate out at room temperature. After filtration under suction, washing with water and drying, 2.38 g (91%) of crude product are obtained. The crude product is purified by column chromatography over silica gel (40–63 μm) using 1:1 hexane/ethyl acetate. This gives 1.56 g (60%) of yellowish crystals which, after recrystallization twice from pentane, give a colorless crystalline solid in a yield of 0.92 g (35%). According to the IR and $^1$H-NMR spectrum, this is compound (3) of the above equation. The second fraction of the column chromatography (0.22 g of the crystalline solid) is likewise recrystallized from pentane, and colorless crystals are obtained in a yield of 0.18 g (7%). According to the IR and $^1$H-NMR spectrum, this is compound (4).

Identification of compound (3):
Melting point: 34° C.; TLC; IR and $^1$H-NMR spectrum Identification of compound (4):
Melting point: 55° C.; TLC; IR and $^1$H-NMR spectrum

EXAMPLE 2

Preparation of the novel compound (5) according to the equation

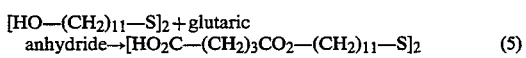

$$[\text{HO—(CH}_2)_{11}\text{—S}]_2 + \text{glutaric anhydride} \rightarrow [\text{HO}_2\text{C—(CH}_2)_3\text{CO}_2\text{—(CH}_2)_{11}\text{—S}]_2 \quad (5)$$

5 g (12.3 mmol) of compound (2) and 2.95 g (25.85 mmol) of glutaric anhydride are stirred for 1 hour at 90° C. An educt is no longer detectable by TLC. The crude product crystallizes on cooling. This is recrystallized twice from an 8:2 mixture of heptane and acetone. 6.61 g (84%) of colorless crystals are obtained.

Identification: TLC; IR and $^1$H-NMR spectrum; melting point: 79°–80° C.;
Elemental analysis:
Calculated C 60.53% H 9.21% O 20.16% S 10.10%:
Found C 60.60% H 9.30% O 20.30% S 10.10%

EXAMPLE 3

Preparation of the novel compound (6) according to the equation

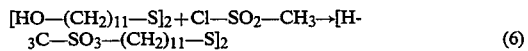

$$[\text{HO—(CH}_2)_{11}\text{—S}]_2 + \text{Cl—SO}_2\text{—CH}_3 \rightarrow [\text{H}_3\text{C—SO}_3\text{—(CH}_2)_{11}\text{—S}]_2 \quad (6)$$

5.0 g (12.3 mmol) of compound (2) and 2.74 g (27.0 mmol) of dry triethylamine are dissolved in 27 g of dry dichloromethane, and the solution is cooled to 0° C. 2.95 g (25.7 mmol) of methanesulfonyl chloride, dissolved in 4 g of dry dichloromethane, are then slowly added dropwise. After the end of the dropwise addition, the mixture is allowed to reach room temperature and is stirred for 2 hours at room temperature. It is filtered over silica gel, and the filtrate is diluted with ethyl acetate, extracted twice by shaking with water and separated in a separating funnel. The organic phase is dried over sodium sulfate, and the solvents are removed in a rotary evaporator. The residue is recrystallized twice from a 7:3 mixture of heptane and ethyl acetate. 4.35 g (63%) of colorless crystals are obtained.

Identification: TLC; IR and $^1$H-NMR spectrum; melting point: 69°–73° C.

EXAMPLE 4

Preparation of the novel compound (7) according to the equation

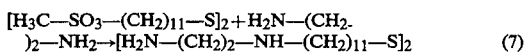

$$[H_3C\text{—}SO_3\text{—}(CH_2)_{11}\text{—}S]_2 + H_2N\text{—}(CH_2)_2\text{—}NH_2 \rightarrow [H_2N\text{—}(CH_2)_2\text{—}NH\text{—}(CH_2)_{11}\text{—}S]_2 \quad (7)$$

2.0 g (3.55 mmol) of compound (6), 2.45 g (40.7 mmol) of ethylenediamine and 8 g of ethanol are refluxed for 3 hours. An educt is no longer detectable in the TLC. The mixture is allowed to cool, 0.4 g of sodium hydroxide is added, stirring is carried out for 30 minutes at room temperature and the mixture is extracted three times by shaking with 40 g of dichloromethane each time. The organic phase is separated off and dried over sodium sulfate and the dichloromethane is removed in a rotary evaporator. 1.3 g of solid are obtained, which gives a colorless crystalline solid in a yield of 0.87 g (51%) after recrystallization from hexane.

Identification: TLC; IR and $^1$H-NMR spectrum; melting point: 68°–74° C.

Compound (7) has the particular property binding heavy metal ions, for example Cu, Cd, Hg, Ni, Pb, Zn, Pd, Rh and others. Because of the good solubility of the complexes of (7) with these heavy metals in organic solvents, for example ethyl acetate, chloroform, dichloromethane, diethyl ether and others, compound (7) is suitable for extracting the stated heavy metals from aqueous solution into the organic phase. Furthermore, monomolecular layers of (7) on sensor surfaces are suitable for detecting the stated heavy metal ions. (7) can even be used for producing reversible sensors, since compound (7) can be regenerated from its heavy metal complexes by adding an acid and then adding an alkali.

EXAMPLE 5 a) Preparation of the compound (8) according to the formula

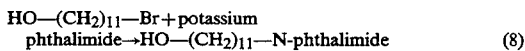

$$HO\text{—}(CH_2)_{11}\text{—}Br + \text{potassium phthalimide} \rightarrow HO\text{—}(CH_2)_{11}\text{—}N\text{-phthalimide} \quad (8)$$

24.33 g (0.131 mol) of potassium phthalimide are suspended in 236 g of dimethylformamide. 30.0 g (0.119 mol) of 11-bromoundecanol are added and stirring is carried out for 3 hours at 70° C. The mixture is allowed to cool and is poured into 600 g of water, the crude product being precipitated. After filtration under suction and drying, recrystallization is effected from 270 g of an 8:2 mixture of heptane and ethanol. 33.2 g (88%) of colorless crystals are obtained.

Identification: TLC; IR and $^1$H-NMR spectrum; melting point: 82°–84° C.

b) Preparation of the compound (9) according to equation

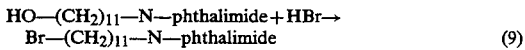

$$HO\text{—}(CH_2)_{11}\text{—}N\text{-phthalimide} + HBr \rightarrow Br\text{—}(CH_2)_{11}\text{—}N\text{-phthalimide} \quad (9)$$

24 g (93 mmol) of 47 percent strength aqueous hydrobromic acid and 3.0 g (31 mmol) of concentrated sulfuric acid are added to 10.0 g (31 mmol) of compound (8). Refluxing is carried out for 4 hours and the mixture is allowed to stand overnight at room temperature. The aqueous acidic solution is removed from the precipitated crystals by means of a pipette, and the crystals are washed acid-free with water. After drying and recrystallization from hexane, 10.0 g (85%) of crystalline solid are obtained.

Identification: TLC; IR and $^1$H-NMR spectrum; melting point: 54° C.

c) Preparation of the compound (10) according to the equation

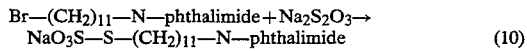

$$Br\text{—}(CH_2)_{11}\text{—}N\text{-phthalimide} + Na_2S_2O_3 \rightarrow NaO_3S\text{—}S\text{—}(CH_2)_{11}\text{—}N\text{-phthalimide} \quad (10)$$

20.0 g (52.6 mmol) of compound (9), 13.05 g (52.6 mmol) of sodium thiosulfate pentahydrate, 65 g of water and 52 g of ethanol are refluxed for 6 hours. An educt is no longer detectable in the TLC. The mixture is allowed to cool, and the product is filtered off under suction and recrystallized from ethanol to give 16.9 g (74%) of colorless crystals.

Identification: TLC; IR and $^1$H-NMR spectrum; melting point: 127°–129° C.

d) Preparation of the novel compound (11) according to the equation

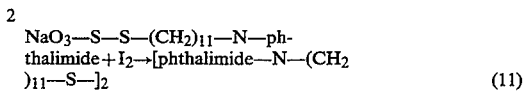

$$2\ NaO_3\text{—}S\text{—}S\text{—}(CH_2)_{11}\text{—}N\text{-phthalimide} + I_2 \rightarrow [\text{phthalimide}\text{—}N\text{—}(CH_2)_{11}\text{—}S\text{—}]_2 \quad (11)$$

11.45 g (26.3 mmol) of compound (10) are dissolved in 28 g of ethanol and 35 g of water, and the solution is heated to the boil. 3.5 g (13.8 mmol) of iodine, dissolved in 20 g of ethanol, are added dropwise to the boiling solution, and stirring is carried out for a further 15 minutes after the end of the dropwise addition. Neutralization is effected with sodium carbonate, the mixture is allowed to cool and the iodine color is eliminated with a little aqueous sodium disulfite solution. The crude product crystallizes out overnight at room temperature. It is filtered off under suction, washed with water, dried, and recrystallized from an 8:2 mixture of heptane and ethyl acetate. 6.7 g (77%) of colorless crystals are obtained.

Identification: TLC; IR and $^1$H-NMR spectrum; melting point: 60°–62° C.;
Elemental analysis:
Calculated C 68.64% H 7.88% N 4.21% S 9.64%:
Found C 68.90% H 8.00% N 4.40% S 9.50%

EXAMPLE 6

Preparation of the novel compound (12) according to the equation

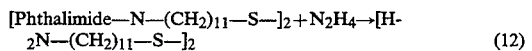

$$[\text{Phthalimide}\text{—}N\text{—}(CH_2)_{11}\text{—}S\text{—}]_2 + N_2H_4 \rightarrow [H_2N\text{—}(CH_2)_{11}\text{—}S\text{—}]_2 \quad (12)$$

1.0 g (1.5 mmol) of compound (11) is dissolved in 8 g of ethanol, and 1.5 g (30 mmol) of hydrazine hydrate are added. Stirring is carried out for 5 hours at room temperature, a precipitate being formed. An adduct is no longer detectable in the TLC. 1.5 g of NaOH, dissolved in 15 g of water, are added, after which the precipitate dissolves, and the mixture is extracted with ether and the product obtained from the ether phase is recrystallized from 8 g of hexane. 0.38 g (62%) of colorless crystals is obtained.

Identification: TLC; IR and $^1$H-NMR spectrum; melting point: 69°–72° C.

EXAMPLE 7 a) Preparation of the compound (13) according to the equation $$HO_2C-(CH_2)_{10}-Br + Na_2S_2O_3 \rightarrow HO_2C-(CH_2)_{10}-S-SO_3Na \quad (13)$$

18.72 g (70.6 mmol) of 11-bromoundecanoic acid, 17.70 g (71.3 mmol) of sodium thiosulfate pentahydrate, 50 g of water and 40 g of ethanol are refluxed for 3 hours. Thereafter, the mixture is cooled to 0° C. and the crystalline crude product is filtered off under suction. Recrystallization from ethanol gives 15.19 g (67%) of colorless crystals.

Identification: TLC; IR and $^1$H-NMR spectrum; melting point: 127° C. (decomposition).

b) Preparation of the novel compound (14) according to the equation $$2\ HO_2C-(CH_2)_{10}-S-SO_3Na + I_2 + C_2H_5OH \rightarrow [H_3C-H_2C-O_2C-(CH_2)_{10}-S-]_2 \quad (14)$$

2.5 g (7.8 mmol) of compound (13) are dissolved in 32 g of ethanol at the boiling point. A solution of 0.99 g (3.9 mmol) of iodine in 12 g of ethanol is added dropwise to the boiling solution, and stirring is carried out for a further 15 minutes after the end of the dropwise addition. The solvent is removed in a rotary evaporator and the residue is taken up in 27 g of ethyl acetate and 30 g of water. The organic phase is separated off, washed again with 30 g of water and then with a solution of 1 g of sodium disulfite in 40 g of water, the iodine color disappearing, and dried over sodium sulfate. The solvent is removed in a rotary evaporator and the remaining residue is recrystallized from methanol. 1.33 g (70%) of colorless crystals are obtained.

Identification: TLC; IR and $^1$H-NMR spectrum; melting point: 47° C.;
Elemental analysis:
Calculated C 63.63% H 10.27% S 13.07%
Found C 63.90% H 10.10% S 13.10%

EXAMPLE 8 a) Preparation of compound (15) according to the equation $$HO-(CH_2)_{11}-Br + Na_2SO_3 \rightarrow HO-(CH_2)_{11}-SO_3Na \quad (15)$$

25.1 g (0.1 mol) of 11-bromoundecanol and 13.9 a (0.11 mol) of sodium sulfite in 50 g of water are refluxed for 10 hours. The product crystallizes out on cooling to room temperature and is filtered off under suction, stirred for 1 hour in 72 g of ether, filtered off under suction again and recrystallized from water. Drying at 60° C. under reduced pressure gives 19.2 g (70%) of colorless crystals.

Identification: TLC; IR and $^1$H-NMR spectrum; melting point: 230°-235° C.

b) Preparation of the compound (16) according to the equation $$HO-(CH_2)_{11}-SO_3Na + HBr \rightarrow Br-(CH_2)_{11}-SO_3H \quad (16)$$

40.15 g (233.2 mmol) of 47 percent strength aqueous hydrogen bromide solution and 5.83 g (58.3 mmol) of concentrated sulfuric acid are added to 16.0 g (58.3 mmol) of compound (15) and refluxing is carried out for 5 hours, the mixture being dark. The crude product crystallizes out on cooling. Recrystallization from 70 g of water gives 9.5 g (52%) of crystalline solid which contains dark impurities. Further recrystallization from 360 g of ethanol gives 7.5 g (41%) of colorless crystals.

Identification: TLC; IR and $^1$H-NMR spectrum; melting point: 176° C. (decomposition)

c) Preparation of the novel compound (17) according to the equation $$Br-(CH_2)_{11}-SO_3H + Na_2S_2O_3 \rightarrow NaO_3S-S-(CH_2)_{11}-SO_3Na;$$

$$2\ NaO_3S-S-(CH_2)_{11}-SO_3Na + I_2 \rightarrow [NaO_3S-(CH_2)_{11}-S-]_2 \quad (17)$$

5.0 g (15.8 mmol) of compound (16) and 4.12 g (16.6 mmol) of sodium thiosulfate pentahydrate are refluxed in 30 g of water for 5 hours. An educt is no longer detectable in the TLC. A solution of 2.3 g mmol) of iodine in ethanol is then added dropwise to the boiling solution and stirring is carried out for 15 minutes after the end of the dropwise addition. Neutralization is effected with sodium carbonate, the mixture is allowed to cool and the solution is decolorized with sodium disulfite. The product is precipitated on cooling. Recrystallization from 35 g of a mixture of ethanol and water in a ratio of 3:1 gives 2.85 g (67%) of colorless crystals.

Identification: TLC; IR spectrum; melting point: 240° C. (decomposition)

EXAMPLE 9

Preparation of the novel compound (18) according to the equation $$[NaO_3S-(CH_2)_{11}-S-]_2 + HCl \rightarrow [HO_3S-(CH_2)_{11}-S-]_2 \quad (18)$$

2.0 g (3.45 mmol) of compound (17) are boiled briefly in 60 g of concentrated hydrochloric acid. The precipitate which separates out on cooling is filtered off under suction, washed with cold ethanol and recrystallized from a mixture of water and ethanol in a ratio of 1:1.

Identification: TLC; IR and $^1$H-NMR spectrum

EXAMPLE 10

1) Preparation of the substrate

A chromium layer about 5 nm thick is deposited by vapor deposition on freshly cleaved mica under greatly reduced pressure in order to improve the adhesion of the subsequent noble metal layer. A gold or silver layer about 100 nm thick is then applied by vapor deposition. Instead of the mica, other substrates, for example silicon wafers, glass, quartz glass, etc., may also be used. The substrates prepared in this manner are referred to below as gold or silver substrates, regardless of the substrate material which is under the gold or silver layer. The noble metal layers obtained by the vapor deposition process are polycrystalline. As soon as the freshly prepared gold or silver substrates come into contact with air, they adsorb hydrophobic impurities from the air. This is evident from the increase in the contact angle with a water drop, until a constant end value is obtained at a contact angle of 85°-90°. The hydrophobic impurities do not interfere with the chemisorption of the novel disulfides. The high affinity of the sulfur in the disulfides for gold and silver displaces the impurities from the gold or silver surface.

2) Preparation of the immersion bath solutions

The type of solvent is not critical for chemisorption of the disulfides. The solvent should merely ensure adequate solubility of the disulfides. Very polar disulfides, such as compounds (17) and (8), are dissolved in water, polar disulfides, such as compounds (12), (7) and (5), are dissolved in ethanol and nonpolar disulfides, such as compounds (3), (4), (6) and (11), are dissolved in ethyl acetate or heptane. The concentration of the disulfide solutions may vary within a wide range without adversely affecting the chemisorption of the disulfides onto the gold or silver substrates. Chemisorbed disulfide layers of constant quality are obtained in the concentration range from $10^{-2}$ to $10^{-4}$ mol per liter.

3) Preparation of the monomolecular disulfide layers

Gold or silver substrates are immersed in immersion bath solutions of the disulfides, chemisorption of the disulfides onto the gold or silver surface taking place spontaneously. Immersion times of about 17 hours give very dense disulfide layers having a high molecular order within the layer. Longer immersion times do not have an adverse effect. Immersion times of from 5 to 15 minutes also give chemisorbed disulfide layers but the surface occupancy is not complete in all cases. Even with an immersion time of only 1 minute, chemisorbed disulfide layers on gold or silver substrates are detectable by the changes in the contact angle.

After the immersion process, the coated gold or silver substrates are removed from the immersion bath and washed with pure solvent in order to remove excess disulfide material which has not been chemisorbed onto the gold or silver surface. Washing ensures that only a monomolecular, firmly chemically bonded disulfide layer remains on the gold or silver substrate.

4) Identification of the monomolecular disulfide layers Contact angle measurements:

Changes in the contact angle of coated gold or silver substrates compared with uncoated ones indicate the presence of a disulfide layer. Disulfides having terminal polar groups produce hydrophilic surfaces on the substrates (small contact angle). Disulfides having terminal nonpolar groups produce hydrophobic surfaces (large contact angle). This shows clearly that the monomolecular disulfide layers modify the wetting properties of the substrates. Thus, hydrophobic, oleophobic and hydrophilic gold or silver surfaces can be produced by simple immersion. The results are summarized in the Table below.

| Disulfide | Contact Angle ($H_2O$) | |
|---|---|---|
| | Gold | Silver |
| (3) [Br—$(CH_2)_{11}$—S—]$_2$ | 82° | 78° |
| (11) [Phthalimide-N—$(CH_2)_{11}$—S—]$_2$ | 24° | 73° |
| (12) [$H_2$N—$(CH_2)_{11}$—S—]$_2$ | 64° | 67° |
| (4) Br—$(CH_2)_{11}$—S—S—$(CH_2)_{11}$—OH | 61° | 71° |
| (7) [$H_2$N—$(CH_2)_2$—NH—$(CH_2)_{11}$—S—]$_2$ | 59° | |
| (6) [$H_3$C—$SO_3$—$(CH_2)_{11}$—S—]$_2$ | 55° | 65° |
| (2) [HO—$(CH_2)_{11}$—S]$_2$ | 42° | 47° |
| (5) [$HO_2$C—$(CH_2)_3$—$CO_2$—$(CH_2)_{11}$—S—]$_2$ | 44° | 42° |
| (17) [$NaO_3$S—$(CH_2)_{11}$—S—]$_2$ | <10° | <10° |

Grazing incidence IR spectroscopy (GIR):

GIR spectra of chemisorbed monomolecular layers of the novel disulfides on gold or silver substrates show the typical vibrations for $CH_2$ groups at 2919 and 2849 $cm^{-1}$.

The disulfide layers have extremely high thermal stability. Heating up to 150° C. results in no desorption or destruction of the layers.

Electrochemical impedance spectroscopy (EIS):

EIS spectra of chemisorbed monomolecular layers of the novel disulfides on gold or silver substrates indicate that the layers are very dense and are impermeable in particular to aqueous electrolytes. Accordingly, the layers are pore-free and act as corrosion inhibitors. Furthermore, they are stable to aqueous electrolytes, i.e. there is no delamination or destruction of the disulfide layers in the course of time.

We claim:

1. A disulfide of the formula (I)

$$X^1—(CH_2)_n—S—S—(CH_2)_n—X^2 \qquad (I)$$

where $X^1$ and $X^2$ are identical to one another and are each —Br, phthalimido, —$NH_2$, —OOC—$(CH_2)_3$—COOH, —$OSO_2$—$CH_3$, —NH—$(CH_2)_2$—$NH_2$, —$SO_3$H or —$SO_3^-M^+$ in which $M^+$ is $Li^+$, $Na^+$ or $K^+$, and n is an integer from 11 to 13, or $X^1$ is —OH and $X^2$ is —Br and n is from 11 to 13, or $X^1$ and $X^2$ are each —COO—$CH_2$—$CH_3$ and n is from 11 to 13.

2. A disulfide of the formula (I) as defined in claim 1 where $X^1$ and $X^2$ are identical to one another and are each phthalimido, —$OSO_2$—$CH_3$, or —$SO_3$H or $SO_3M^1$ in which $M^1$ is $Li^+$, $Na^+$ or $K^+$.

* * * * *

UNITED STATES PATENT AND TRADEMARK OFFICE
CERTIFICATE OF CORRECTION

PATENT NO.: 5,347,015

DATED: September 13, 1994

INVENTOR(S): KELLER et al.

It is certified that error appears in the above-identified patent and that said Letters Patent is hereby corrected as shown below:

Column 16, claim 1, line 40, "NH2" should read --$NH_2$--.

Signed and Sealed this

First Day of November, 1994

Attest:

BRUCE LEHMAN

Attesting Officer

Commissioner of Patents and Trademarks